United States Patent
Chen

(10) Patent No.: US 9,526,819 B2
(45) Date of Patent: Dec. 27, 2016

(54) VENTRICULAR ASSIST DEVICE CONTROLLER WITH INTEGRATED POWER SOURCE

(71) Applicant: CH Biomedical (USA) Inc., Torrance, CA (US)

(72) Inventor: Chen Chen, Santa Barbara, CA (US)

(73) Assignee: CH BIOMEDICAL (USA), INC., Torrance, CA (US)

( * ) Notice: Subject to any disclaimer, the term of this patent is extended or adjusted under 35 U.S.C. 154(b) by 174 days.

(21) Appl. No.: 14/497,399

(22) Filed: Sep. 26, 2014

(65) Prior Publication Data

US 2016/0089483 A1   Mar. 31, 2016

(51) Int. Cl.
| | |
|---|---|
| *A61N 1/362* | (2006.01) |
| *A61M 1/12* | (2006.01) |
| *A61M 1/10* | (2006.01) |
| *G05B 15/02* | (2006.01) |

(52) U.S. Cl.
CPC .......... *A61M 1/127* (2013.01); *A61M 1/1086* (2013.01); *G05B 15/02* (2013.01); *A61M 1/122* (2014.02); *A61M 2205/3538* (2013.01); *A61M 2205/50* (2013.01); *A61M 2205/8212* (2013.01); *A61M 2205/8243* (2013.01)

(58) Field of Classification Search
CPC .............................. A61M 1/122; A61M 1/127
USPC ......................................................... 600/16
See application file for complete search history.

(56) References Cited

U.S. PATENT DOCUMENTS

| | | | |
|---|---|---|---|
| 2011/0218383 A1* | 9/2011 | Broen | A61M 1/127 600/16 |
| 2011/0218384 A1 | 9/2011 | Bachman et al. | |
| 2012/0154143 A1 | 6/2012 | D'Ambrosio | |
| 2014/0066689 A1 | 3/2014 | Rainier et al. | |

OTHER PUBLICATIONS

PCT International Search Report dated Aug. 14, 2015; 2 pages.
PCT Written Opinion of the International Search Authority; dated Jul. 24, 2015; 11 pages.

* cited by examiner

*Primary Examiner* — Amanda Patton
*Assistant Examiner* — Philip C Edwards
(74) *Attorney, Agent, or Firm* — Seyfarth Shaw LLP

(57) ABSTRACT

An extra-corporeal controller unit for an implantable ventricular assist device (VAD) includes control circuitry integrated with a rechargeable power source without including any power cables between the control circuitry and the rechargeable power source. The rechargeable power source includes two or more rechargeable batteries configured in respective battery modules. The battery modules are configured for removable installation in a housing of the controller unit. Mating power connectors are integrated in the battery modules and the housing. The mating connectors are configured to couple each battery to the control circuitry whenever the respective battery module containing the battery is installed in the housing. An energy storage unit may be permanently included in the controller unit and configured to remain fully charged and provide power to the VAD when the battery modules are removed.

20 Claims, 14 Drawing Sheets

VENTRICULAR ASSIST DEVICE CONTROLLER WITH INTEGRATED POWER SOURCE

FIELD OF TECHNOLOGY

The present disclosure relates to implantable ventricular assist devices (VADs) and more particularly to extra-corporeal control circuitry and power components for a VAD.

BACKGROUND

Ventricular assist devices are blood pumps, which assist blood circulation when a subject's heart is incapable of providing adequate blood circulation. FIG. 1 illustrates a conventional ventricular assist device (VAD) with extra-corporeal power and control components. The VAD 2 is implanted in a subject's body 4 near the heart 3. The VAD 2 is coupled by a percutaneous cable 6 to extra-corporeal components including a controller 8 and a power source. The power source may include and alternating current (AC) power source (not shown) and a pair of rechargeable batteries 10, 12, for example.

Power cables 14, 16 couple the power sources to the controller 8. Conventionally, one end of each power cable 14, 16 includes a connector coupled to the power source and another end of each power cable 14, 16 includes another connector coupled to the controller 8. Normally, more than one rechargeable battery 10, 12 are coupled to a VAD controller 8, as shown, to provide improved safety. During operation of the VAD 2, when the controller 8 that is supplying power to the VAD 2 is disconnected from an AC power cable (not shown), two batteries 10, 12 remain coupled to the controller 8 to ensure that sufficient and continuous power is provided to the VAD 2. When one of the rechargeable batteries 10, 12 (e.g., battery 10) is disconnected from the controller 8 to be charged, the other battery (e.g., battery 12) remains connected to the controller 8 and provide uninterrupted power to the controller 8 and blood pump 2. Within a short time after one battery 10 is disconnected from the controller 8, a fully charged standby battery is usually connected to the controller 8 via connecting cables 14. The system then resumes operation with at least two power sources connected to the controller.

Normally, the two batteries 10, 12 are substantially similar or identical with the same capacity, size and weight. This type of conventional system generally draws power from one battery (e.g. 10) at a time until it is discharged to certain level. Then the system urges the patient to replace the substantially discharged battery with a fully-charged standby battery. During this period, the second battery (e.g. 12), which is connected to the controller, stands idle and remains at full capacity. However, in the conventional system, the time interval between changing batteries is usually determined by the life time of a single battery, rather than the sum of the life time of the two batteries. For example, if one battery 10 lasts five hours, then the patient is typically instructed to change battery every five hours, even though the second battery 12 is still capable of maintaining the system in normal operation for the next five hours. As a result, a patient using the conventional system generally carries a redundant battery of the same size and weight as an operational battery all the time. This causes inconvenience and burden that detrimentally affects the patients' normal activities.

The conventional configuration as shown in FIG. 1, includes at least three extra-corporeal components including the controller 8, a first rechargeable battery 14 coupled to the controller 8 and a second rechargeable battery 16 separately coupled to the controller 8. These extra-corporeal components, which are carried by the subject, severely limit the subject's mobility and comfort. Moreover, the power cables 14, 16 that are coupled between controller 8 and batteries 10, 12 are prone to mechanical wear and include connectors that may eventually fail after being repeatedly connected and disconnected to the controller 8 and batteries 10, 12, for example, many times in a day every day. It is also possible that a connector of a power cable 14, 16 may loosen or that the power cable may become completely disconnected from the battery 10, 12 or controller 8. These failure modes impose a potentially fatal risk of power interruptions and/or control signal interruptions to a VAD that could prevent the VAD from operating.

SUMMARY

Aspects of the present disclosure include an extra-corporeal controller unit for an implantable ventricular assist device (VAD) in which rechargeable batteries and control circuitry are integrated into a single housing. The extra-corporeal controller unit is configured for coupling to the VAD via a percutaneous cable or a transcutaneous energy/signal transmission mechanism. According to the present disclosure, the control unit includes control circuitry integrated with a rechargeable power source without including any power cables between the control circuitry and the rechargeable power source.

According to another aspect of the present disclosure, the rechargeable power source includes two or more rechargeable batteries configured in respective battery modules. The battery modules are configured for removable installation in a housing of the controller unit. Mating power connectors are integrated in the battery modules and the housing. The mating connectors are configured to couple each battery to the control circuitry and/or to the percutaneous cable or the transcutaneous energy/signal transmission mechanism whenever the respective battery module containing the battery is installed in the housing.

These and other features, aspects and advantages of the present disclosure will be better understood with reference to the following drawings, description and claims.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

Figure 1:
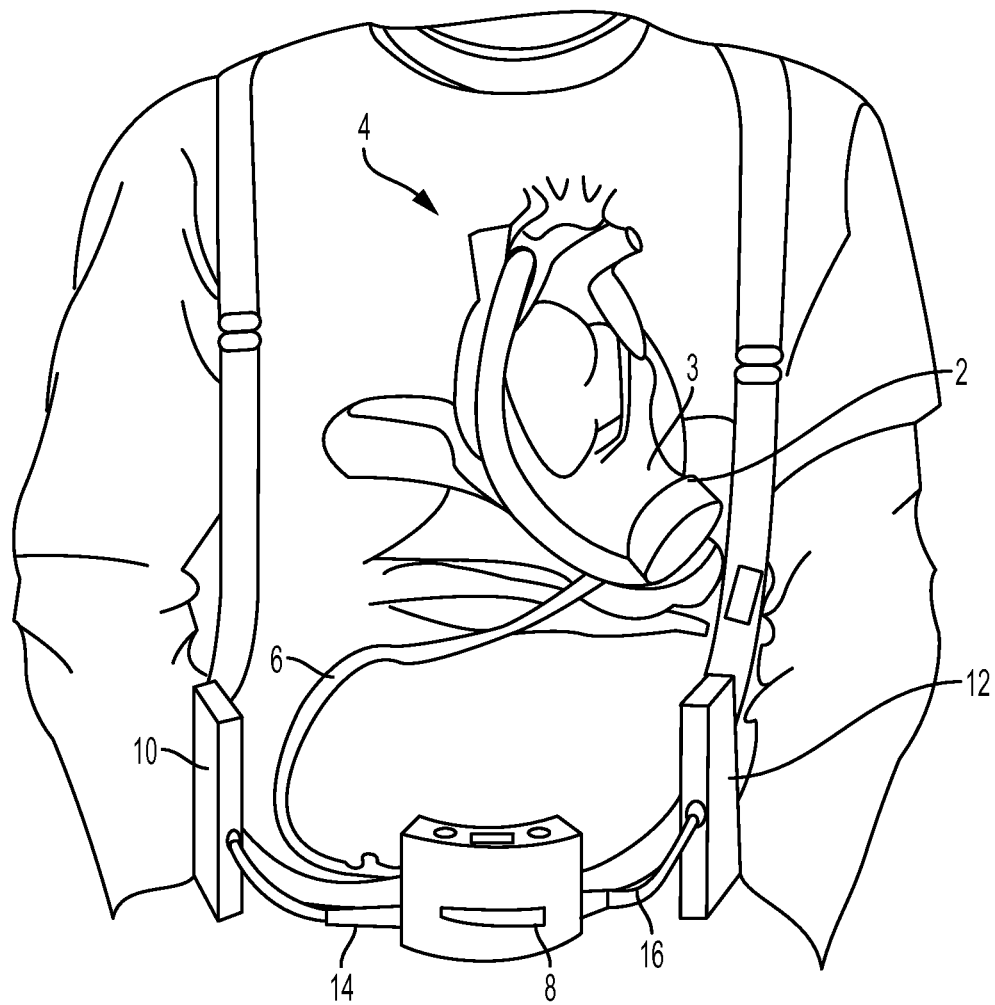
FIG. 1 is an illustration of a conventional ventricular assist device with extra-corporeal power and control components.

It should be understood that the comments included in the notes as well as the materials, dimensions and tolerances discussed therein are simply proposals such that one skilled in the art would be able to modify the proposals within the scope of the present disclosure.

DETAILED DESCRIPTION OF THE DISCLOSURE

While aspects of the present disclosure include embodiments in many different forms, there is shown in the drawings, and will herein be described in detail, a preferred embodiment of the invention with the understanding that the present application is to be considered as an exemplification of the principles of the disclosure and is not intended to limit the broad aspect of the disclosure to embodiments illustrated.

The following detailed description is of the best currently contemplated modes of carrying out exemplary embodiments of the disclosure. The description is not to be taken in a limiting sense, but is made merely for the purpose of illustrating the general principles of the disclosure, since the scope of the disclosure is best defined by the appended claims.

Various features are described below that can each be used independently of one another or in combination with other features. However, any single feature may not address any of the problems discussed above or may only address one of the problems discussed above. Further, one or more of the problems discussed above may not be fully addressed by any of the features described below.

Figure 2A:
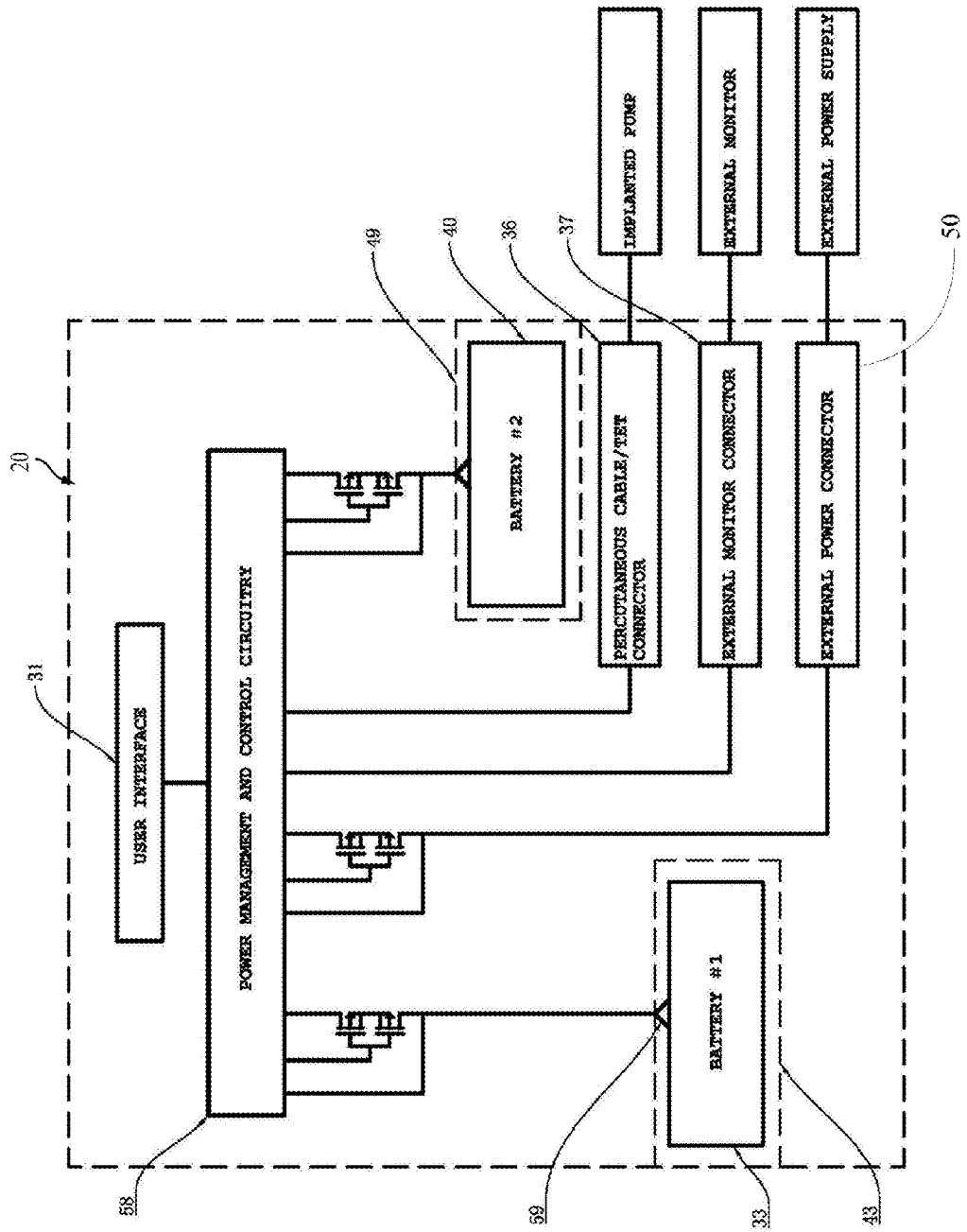
FIG. 2A-2C are system block diagrams illustrating components of a ventricular assist device controller unit according to aspects of the present disclosure.

An extra-corporeal controller unit for an implantable ventricular assist device (VAD), according to an aspect of the present disclosure is described with referring to FIG. 2A. The controller unit 20 includes power management and control circuitry 58 and one or more batteries 33, 40 coupled to the power management and control circuitry 58. The power management and control circuitry 58 controls the implantable VAD and provides power to the VAD via a percutaneous cable or a transcutaneous energy transmission system. The percutaneous cable or the transcutaneous energy transmission system may be connected to the power management and control circuitry 58 via a cable connector 36 on the controller unit 20.

According to an aspect of the present disclosure, the removable batteries 33, 40 are installed in the battery module compartments 43, 49. The control circuitry 58 is connected via connectors 59, 49 to the batteries 33, 40. The batteries 33, 40 are configured to supply power independently to the implanted pump via the control circuitry 58.

According to an aspect of the present disclosure, the control circuitry 58 is coupled to an external monitor connector 37 on the controller unit 20. The control circuitry 58 may be connected to an external monitor via a cable coupled to the external monitor connector 37. The external monitor allows clinicians to adjust operational parameters of the pump, for example the pump rotational speed. According to an aspect of the present disclosure, a user interface 31 on the controller unit 20 is also coupled to the control circuitry 58. The user interface 31 may include one or more control buttons and/or switches and a display, for example. The display may be configured to provide an additional means for monitoring performance of the VAD.

The control circuitry 58 may be coupled to an external power connector 50, which in turn connects to an external power supply, such as an adapter from an AC power source. The external power connector 50 and the external monitor connector 37 may be combined into a single connector on the controller unit 20 for compactness of the controller unit. When these connectors are combined, either the external monitor or the external power supply can be connected to the controller 20 at a time, but they are not to be connected simultaneously. By coupling to the external power connector, the control circuitry 58 can choose the external power source as a power supply for the VAD system, in addition to the other power supplies such as the batteries 33, 40.

When an external power supply is not connected to the controller unit 20, the control circuitry 58 is configured to deliver power to the VAD system from one of the rechargeable batteries, e.g., from battery 33. The power capacity of the battery 33 gradually decreases as energy is consumed for operation of the VAD system. Once the battery 33 is discharged to an extent that its capacity falls below a predetermined capacity level, the control circuitry 58 ceases delivering power from that battery 33 and begins to deliver power from the other battery, e.g., battery 40. In the meantime, the user is prompted to remove the discharged battery 33 from the controller unit 20 for recharging, and quickly replace it with a standby battery that has already been charged to full capacity. According to this aspect of the present disclosure, at least one battery is always installed in the controller unit housing to maintain uninterrupted power supply during the process of battery change.

According to an aspect of the present disclosure, the control circuitry is configured to immediately switch the coupled power source path from one of the batteries 33, 40 to the other if the currently operational battery unexpectedly fails to function normally. Such abnormal functioning may include accidental removal of the operational battery from the controller unit housing 20 by the user, decoupling of the operational battery from the control circuitry 58, or sudden loss of power capacity of the operational battery, for example. According to an aspect of the present disclosure, the control circuitry 58 is configured to detect such abnormal functioning of an operational battery by consistently monitoring the voltage and/or current of the operational battery, or by other commonly known techniques for monitoring battery functionality. When a power failure or abnormal functioning of a currently operational battery is detected, the control circuitry 58 immediately switches the coupled power supply path from the current operational battery to another available battery. The control circuitry 58 includes electronic hardware and/or software that are configured to maintain an uninterrupted power supply to the VAD system during the process of the power supply switching. In one example, as illustrated in FIG. 2A, a switching circuitry is employed to engage or disengage each battery 33, 40 individually under software commands. In addition, a capacitor (not shown) is employed in the booster of the control circuitry to maintain a sufficient voltage level of power source to the system during the switching process.

The rechargeable batteries enclosed in the controller unit are each configured to possess sufficient capacity to provide uninterrupted power supply to the VAD system if they are selected due to the unexpected abnormal functioning of another rechargeable battery in the controller unit. To ensure that this reserve capacity is maintained, the threshold of battery capacity used by the control circuitry for indicating a needed recharge or replacement of a battery is set to a high enough level to include sufficient residual capacity for a short period of operation. This ensures that even when a battery is discharged to a level that triggers a replacement indicator signal and is subject to replacement, it still possesses sufficient capacity to be used as an alternative power supply for a short period of time in case the remaining battery unexpectedly functions abnormally.

Another aspect of the present disclosure is described with reference to FIGS. 2B and 2C in which one or more energy storage units 47 are coupled to and/or integrated with the power management and control circuitry 58 along with one or more rechargeable battery(ies) 33 and/or 40 to provide power to the VAD. Unlike the batteries 33 or 40, the energy storage unit 47 is permanently coupled to the power management and control circuitry 58 and permanently installed inside the controller unit 20. In one example, the energy storage unit 47 may be integrated with the power management and control circuitry 58, for example. The energy storage unit is configured to continuously maintain or seek to maintain an energy level that is at or near its full capacity. For example, the energy storage unit 47 is configured to not supply power whenever a battery 33 or 40, or any other means of power supply coupled to the external power connector 50 is installed and functioning normally to supply power to the VAD. The energy storage unit 47 is configured to release its stored energy and thereby supply power to the VAD only when all of the removable batteries 33 are removed from the extra-corporeal controller unit or not functioning properly and when no other power source is supplying power to the VAD system. According to an aspect of the present disclosure, the energy storage unit is configured to store and release enough energy to allow normal operation of the VAD for a sufficient length of time.

The energy storage unit 47 facilitates safe operation of an extra-corporeal control unit according to an aspect of the present disclosure having only one removable rechargeable battery 33. The energy storage unit 47 provides sufficient power for operating the VAD when the battery 33 is removed from the controller for recharging. Another battery 33 having full capacity is usually very soon installed to the battery module compartment 43. Once the new battery 33 is installed, the energy storage unit 47 is controlled to automatically disengage from supplying power to the VAD and to begin recharging to maintain a charge or energy level that is at or near its full capacity. The energy storage unit 47 can supply power for the VAD and the extra-corporeal control unit 20 in situations when all batteries or other means of power to the VAD and the extra-corporeal control unit fail, such as during accidental removal of batteries or loss of battery capacity. According to an aspect of the present disclosure, the power storage unit 47 is also configured to ensure that an alarm systems has power to function to indicate when all batteries are out of capacity, for example.

According to aspects of the present disclosure, the energy storage unit 47 is not removable from the extra-corporeal control unit. The energy storage unit is configured to continuously maintain a full charge and may be directly integrated into the power management and control circuitry 58. As shown in FIG. 2B, the energy storage unit 47 may be a super capacitor 63, for example. In this example, the super capacitor 63 can be charged by the battery 33 or 40 or other means of power supply to the extra-corporeal controller unit 20, such as an external power source coupled to the external power connector 50. As shown in FIG. 2C, the energy storage unit 47 may be a backup battery 61, for example. In this example, the backup battery 61 can be charged by the battery 33, 40 or other means of power supply to the extra-corporeal controller unit 20, such as an external power source coupled to the external power connector 50.

Figure 2B:
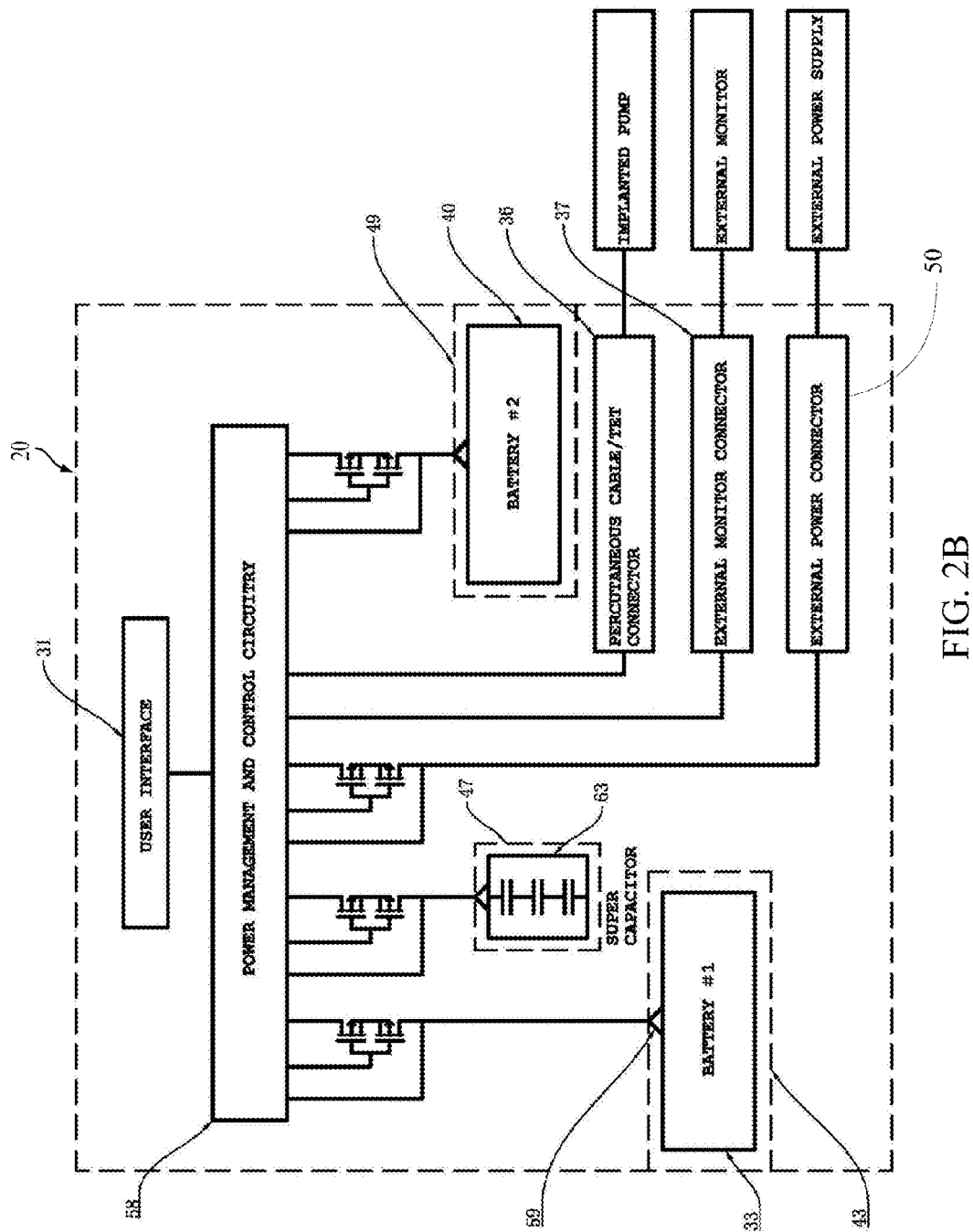
Figure 2C:
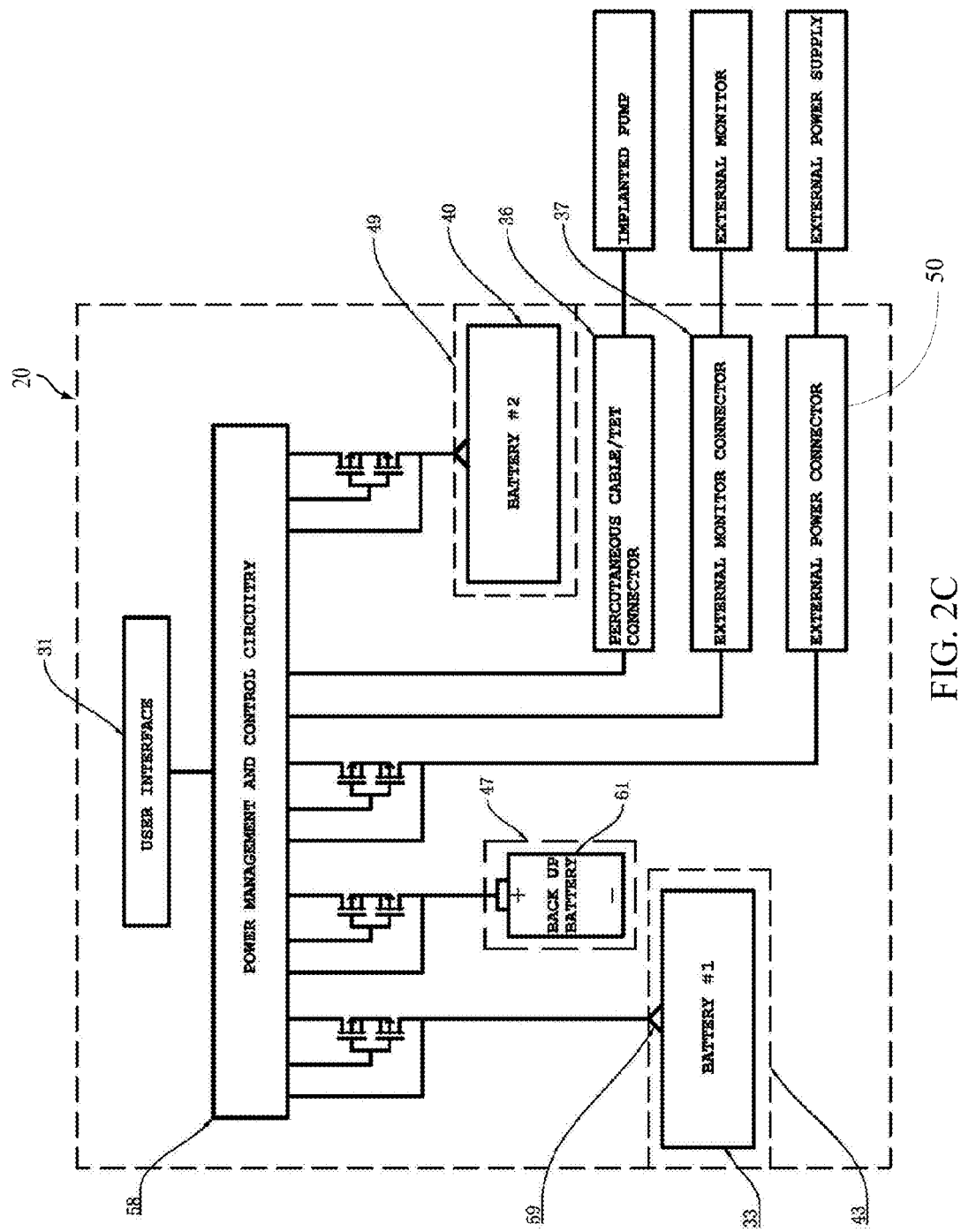

According to an aspect of the present disclosure as illustrated in FIGS. 2A, 2B, and 2C, the batteries 33, 40 may or may not have the same capacity and/or physical characteristics such as size and weight. One of the batteries (e.g. 40) may have significantly less capacity and thus be significantly lighter and/or smaller than the other battery (e.g. 33). To facilitate description, such battery 40 that has less capacity is named the secondary battery and the other battery 33 is named the primary battery. The VAD system is normally operating with the primary battery 33 providing power to the entire system. The secondary battery 40 is configured not to supply power whenever the primary battery 33 or any other means of power supply, e.g. an external power supply through the external power connector 50, is functioning normally. The secondary battery 40 is configured to supply power to the VAD system when the primary battery 33 is removed from the controller unit 20 for recharging, and no any other means of power supply is connected to the controller and functioning normally. Very soon after a primary battery 33 has been removed from the controller unit for recharging, a new primary battery 33 possessing full capacity is quickly installed into the controller unit 20. Once the new primary battery 33 is installed and able to function normally, the power management and control circuitry 58 resumes power supply from the primary battery 33 and disengage the secondary battery 40 from supplying power to the VAD system. The secondary battery 40 is capable of supporting normal operation of the VAD system for a sufficient length of time, e.g. a few tens of minutes. Moreover, once the control circuitry 58 detects that the secondary battery has discharged to a certain capacity level, it prompts the user to replace the secondary battery 40 when the primary battery maintains uninterrupted power supply to the system.

Since the secondary battery 40 is lighter and/or less bulky than the primary battery 33, the controller unit 20 can be made lighter and/or smaller as compared to the configurations that employ a pair of identical batteries 33, 40. The reduction in size and/or weight of the controller unit does not necessarily require the user to replace the rechargeable battery more frequently, because with either of the configurations the duration for battery replacement is equally determined by the life time of one single battery in the controller unit. The duration for battery replacement is determined by the life time of the primary battery when a combination of primary and secondary batteries is used, whereas it is determined by the life time of any of the batteries in the controller unit when two or more identical batteries are used. For example, suppose that a primary battery can provide power for five hours of normal operation of the VAD system before recharging, and a secondary battery can merely provide power for half an hour of operation. With one configuration, if a combination of the primary and secondary batteries is employed, then the user is required to replace battery every five hours. With the other configuration, if two primary batteries are used together, then the user is still required to replace battery every five hours since only one battery is operational. Therefore, the configuration of combined primary and secondary batteries does not require the user to replace battery more frequently.

Another aspect of the present disclosure involves a method of managing the two or more batteries 33, 40 when every battery has substantially similar or identical capacity. According to one such method, once the control circuitry 58 detects that the capacity of one of these batteries, e.g. 33, has fallen below a threshold for recharging, it immediately triggers a warning signal to urge the user to remove the battery 33 from the controller unit and quickly replace it with a new battery that is charged to full capacity.

According to another method of battery management, once the control circuitry 58 detects that the capacity of the operational battery, e.g. 33, has fallen below a first threshold (magnitude A) for recharging, it checks the capacity of the other batteries. If the control circuitry 58 detects that any of these other batteries, e.g. 40, still possesses capacity above a second threshold (magnitude B), which is substantially greater than the first threshold, then the control circuitry 58 disengage the battery 33 and engage the battery 40 as the power source to the VAD system. At the same time, the control circuitry may trigger a reminding signal to the user to suggest change of the discharged battery 33, but does not necessarily urge the patient to do so immediately. After further operation of the VAD system, if the control circuitry 58 detects that the capacity of the operational battery(ies) 40 has fallen below a third threshold (magnitude C), it triggers a warning signal to urge the patient to change the more depleted battery 33, followed by changing the less depleted battery 40. According to aspects of the present disclosure, the level of magnitude C is set to be higher than the threshold A so that after the power capacity of battery 40 falls to level C, the battery 40 is still able to support normal operation of the VAD system for a sufficient length of time, e.g. from a few minutes to an hour, that will allow the user to finish battery change.

The latter method has the advantage of providing a longer time interval before a patient needs to replace a battery, and thus improves the patient's quality of life. For example, if each battery 33, 40 can serve for power supply for five hours before recharging, then with the conventional method, the patient has to change battery once every five hours. However, by using two or more batteries successively according to this aspect of the present disclosure the user can postpone change of the first discharged battery until the next operational battery needs to be replaced for recharging, i.e. after another five hours. The time interval for battery change may be extended further in the same manner if the system carries a third or even more rechargeable batteries.

According to another aspect of the present disclosure, a transcutaneous energy transmission (TET) system includes a first TET unit that is implantable along with a VAD and a second TET unit that is placed outside of the subject's body. Each of the TET units includes a coil that can be inductively coupled to a coil in the other TET unit. By providing high frequency current to the coil in the external TET unit, power and/or control signals are inductively transmitted to the coil in the implanted TET unit. The implanted TET unit provides power and/or control signals from its coil to an implanted VAD.

Figure 3:
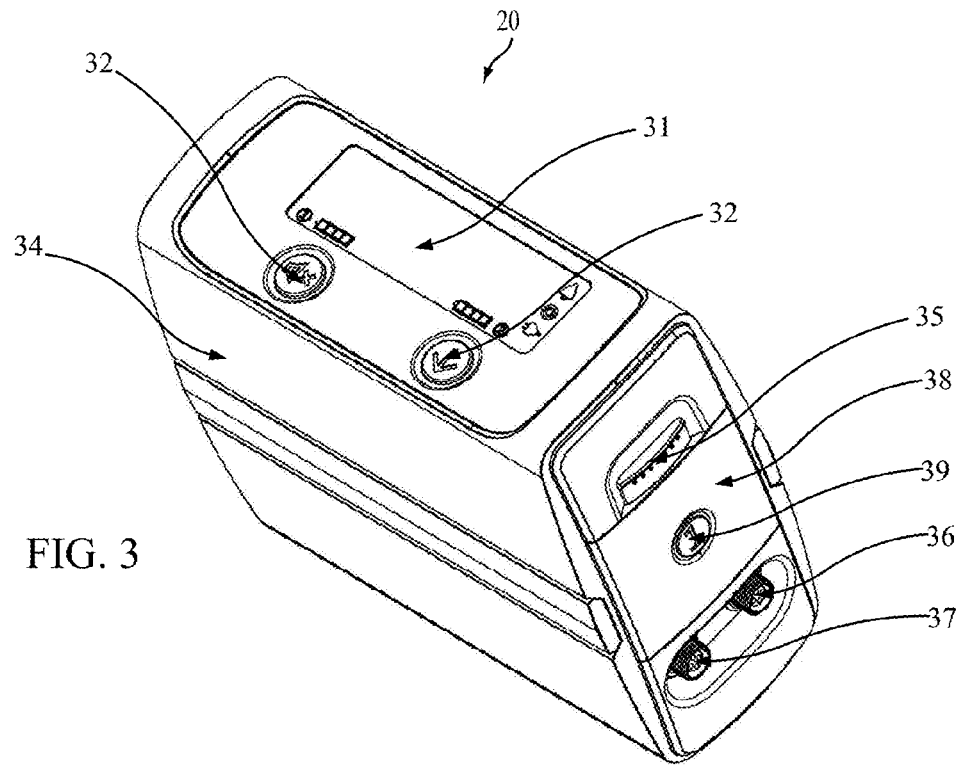
FIGS. 3-6 are illustrations of a ventricular assist device controller unit including integrated battery modules according to an aspect of the present disclosure.
Figure 4:
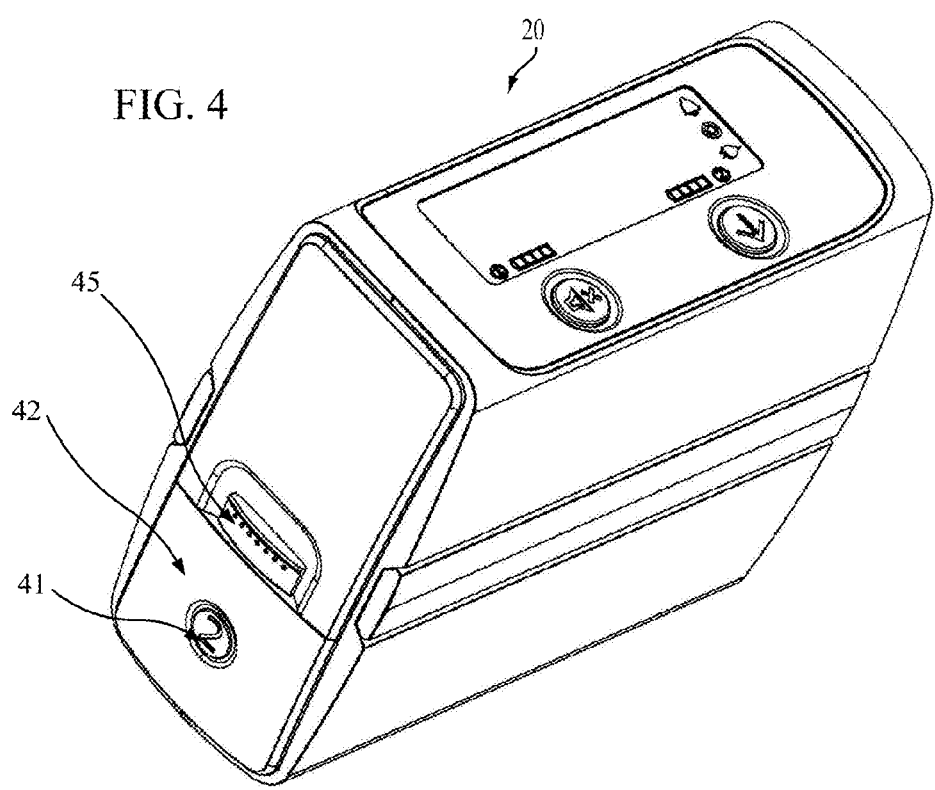
Figure 5:
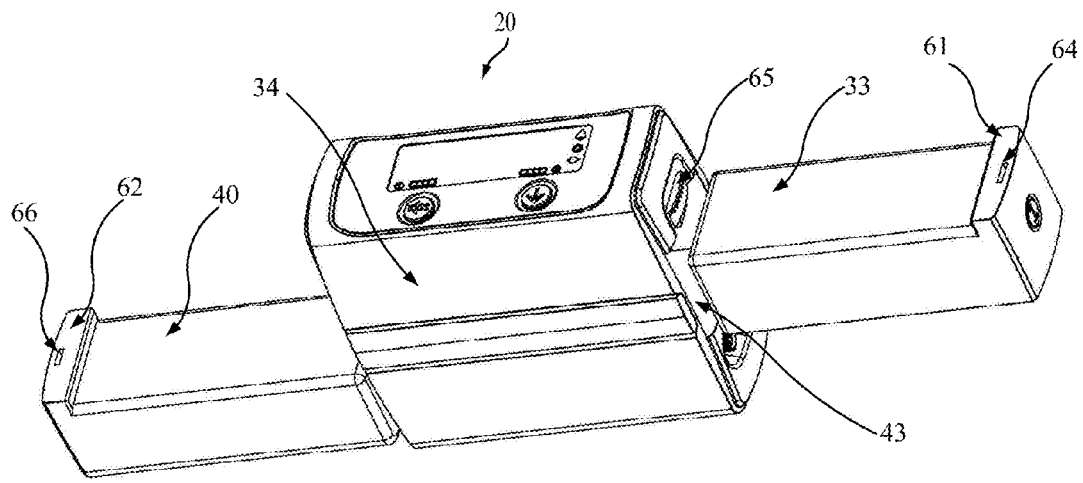

An example of a controller unit 20 according to an aspect of the present disclosure is described with reference to FIGS. 3-6. Referring to FIGS. 3 and 4, the controller unit 20 includes a housing 34 that encloses two battery compartments, which are located behind corresponding battery compartment lids 38, 42. Rechargeable batteries are removably installed in the battery compartments. As illustrated in FIG. 5, the battery modules 33, 40 are removed from their respective battery compartments. According to an aspect of the present disclosure, the battery modules 33, 40 may be easily installed in the housing 34 and removed from the housing 34 without tools. At least one of the battery modules 33, 40 is normally installed in the controller unit 20 at all times to provide sufficient power supply to the VAD and to the control circuitry.

Each battery compartment lid 38, 42 includes a locking mechanism 35, 45 configured to retain a battery within a corresponding battery compartment in the housing 34. According to an aspect of the present disclosure, indicators 39, 41 are located on each of the battery compartment lids 38, 42. The indicators 39, 41 are configured to provide indications, by flickering or beeping for example, when a battery level of one of the batteries is below a preset level for normal operation. A cable connector 36 on the housing 34 is configured to provide a connection to the percutaneous cable or a transcutaneous energy transmission unit that connects to an implanted blood pump. An external monitor connector 37 on the housing is configured to provide a cable connection to an external monitor. The same connector can connect to a cable of an external power supply. A display 31 located on the housing 34 of the controller unit 20 displays operating parameters and status of the VAD system. Control buttons 32 located on the housing 34 of the controller unit 20 facilitate adjustment of certain VAD operating parameters, and/or display options, for example.

According to an aspect of the present disclosure, an internal energy storage unit, in addition to the batteries 33, 40 may be integrated with the power management and control circuitry 58 within the housing 34. The internal energy storage unit is configured to supply power for the control circuitry and for the VAD if the batteries 33, 40 fail to supply power. For example, the internal power storage unit supplies power if all of the batteries 33, 40 are accidentally removed or become discharged. The power storage element is configured to assure that an alarm system, such as indicators 39, 41 are operable when all of the batteries 33, 40 fail or become disconnected or discharged. According to an aspect of the present disclosure, the internal energy storage unit may include a capacitors such as a super capacitor, for example. According to another aspect of the present disclosure, the internal power storage unit may include a backup battery. The backup battery may be configured so that it is replaceable and may be rechargeable, or non-rechargeable, for example.

In one embodiment of the disclosed controller module, a locking mechanism on the housing is configured to engage a lid on a battery module when the battery module is installed in a corresponding battery module compartment of the housing and to retain the battery module within the controller unit. The lid is configured to engage a mating portion of the housing when the battery module is installed in the corresponding battery module compartment. A sealing structure, such as an o-ring or gasket, surrounds each of the battery module compartments. The sealing structure is configured to prevent water from entering a corresponding battery module compartment when a battery module is installed and retained into the battery module compartment by the locking mechanism. The lid also protects the battery and circuit from external interference and wear.

Figure 6:
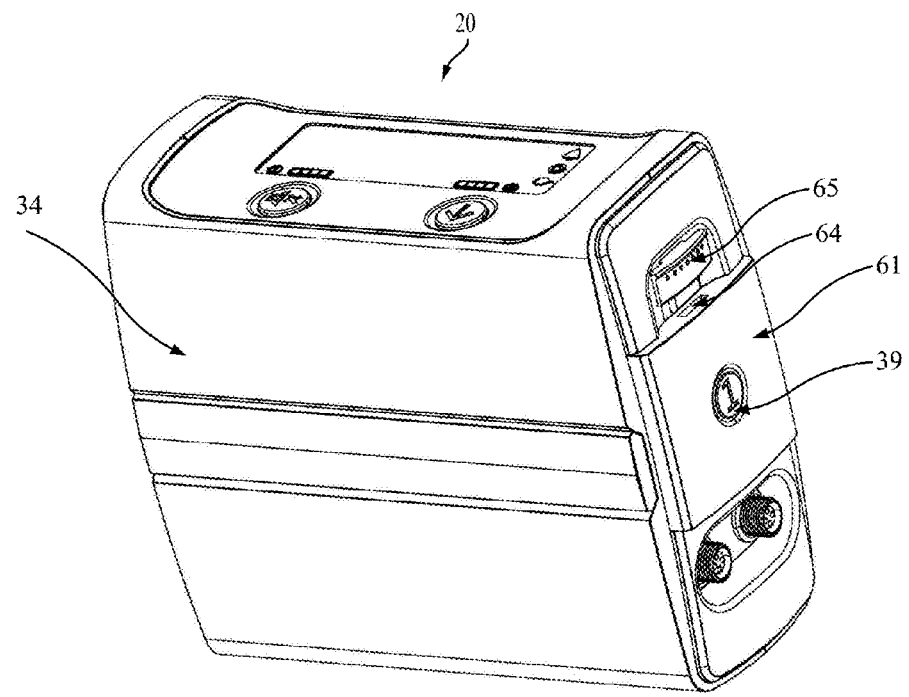

Referring to FIGS. 5 and 6, a battery compartment lid 61, 62 is integrated with the battery modules 33, 40 respectively. According to an aspect of the present disclosure, a groove 64, 66 is made on each battery compartment lid 61, 62, and a locking mechanism corresponding to each groove is installed on the housing 34. When a battery module 33 is completely installed in the corresponding battery compartment 43, as illustrated in FIG. 6, the locking mechanism 65 engages the groove 64 on the battery compartment lid 61 to retain the battery 33 in the battery compartment. The locking mechanism may include a spring-loaded key that enters into the corresponding groove on the battery compartment when the locking mechanism is engaged. The battery module 40 is retained with a substantially identical locking mechanism as the locking mechanism 65, which is installed on the other side of the housing 34 (not shown) and engages groove 66 when the battery module 40 is completely installed in the battery compartment.

Figure 7:
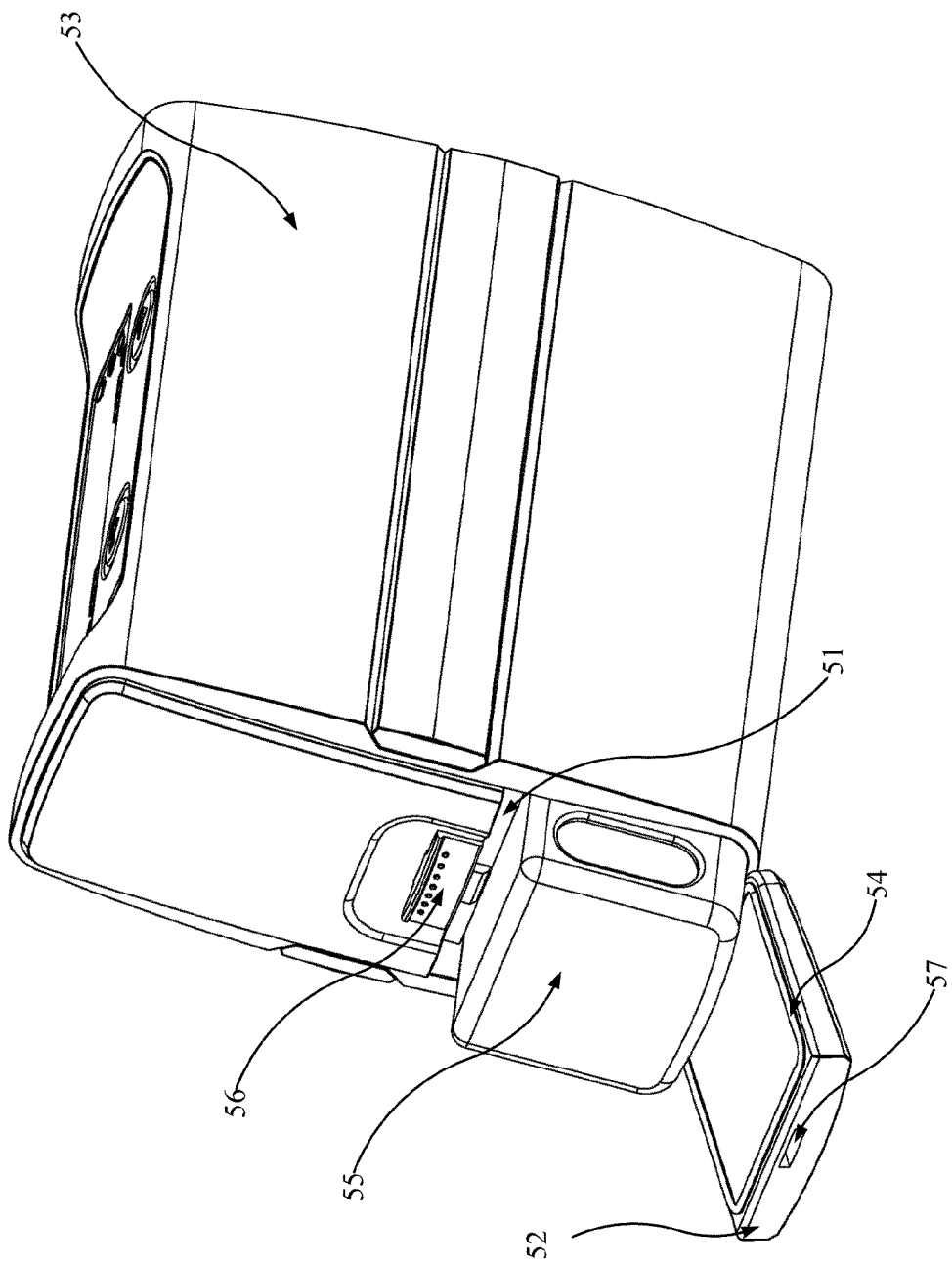
FIG. 7 is an illustration of a ventricular assist device controller unit according to another aspect of the present disclosure.

Another example of a controller unit according to an aspect of the present disclosure is described with reference to FIG. 7. In this example, a battery compartment lid 52 is coupled by a hinge to a housing 53 of the controller unit. After a battery 55 is completely installed in the battery compartment 51, the lid can rotate around the hinge to enclose the battery 55 in the battery compartment 51. A locking mechanism 56 on the housing 53 engages a groove 57 on the lid 52 so that the battery is completely enclosed in the compartment. A sealing structure 54 such as an o-ring or gasket ring 54 is configured on the lid to prevent water from entering the closed battery compartment 51.

Figure 10:
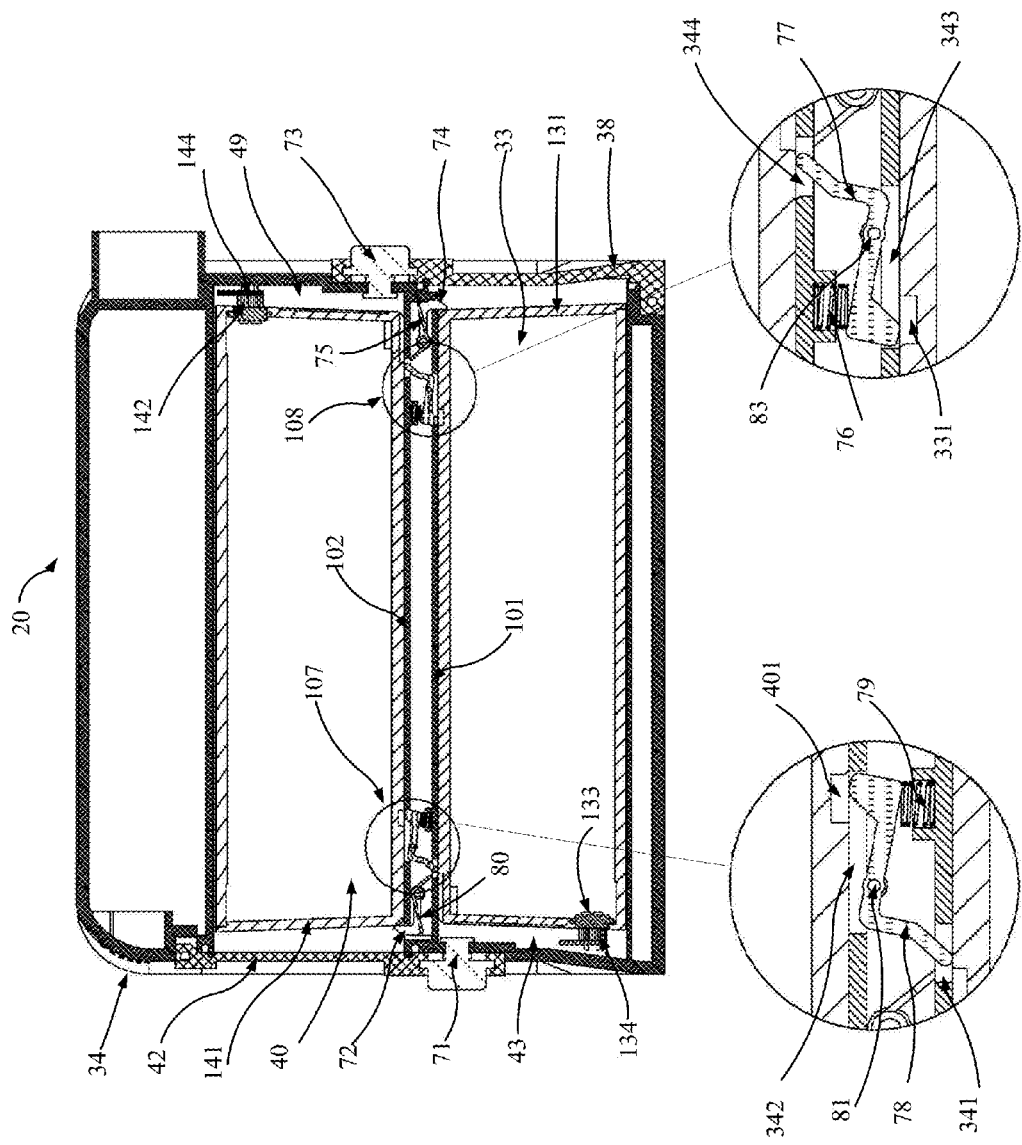
FIGS. 10-14 are cross-sectional illustrations of a ventricular assist device controller unit including an interlocking mechanism for the integrated battery modules according to an aspect of the present disclosure.
Figure 12:
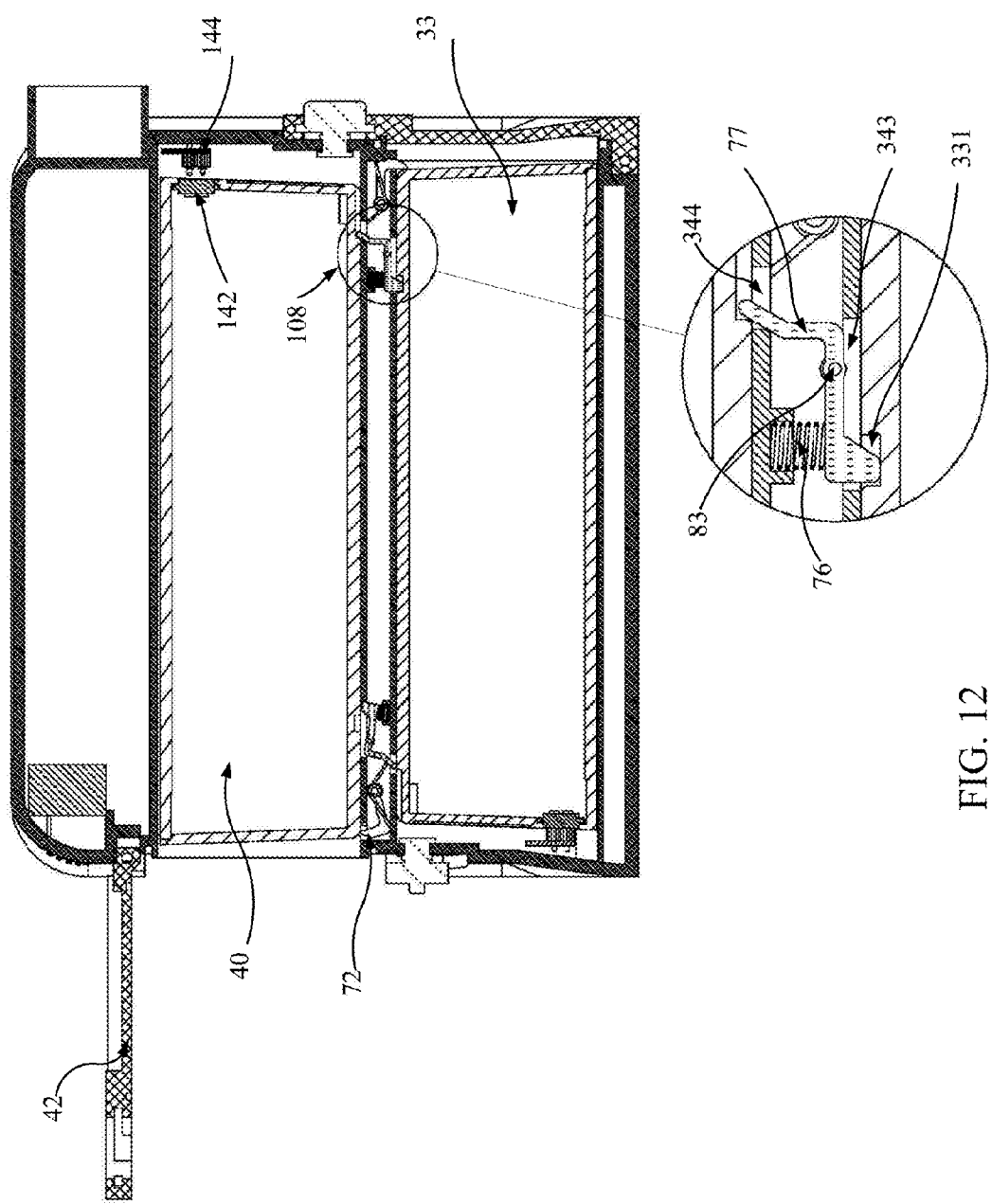
Figure 13:
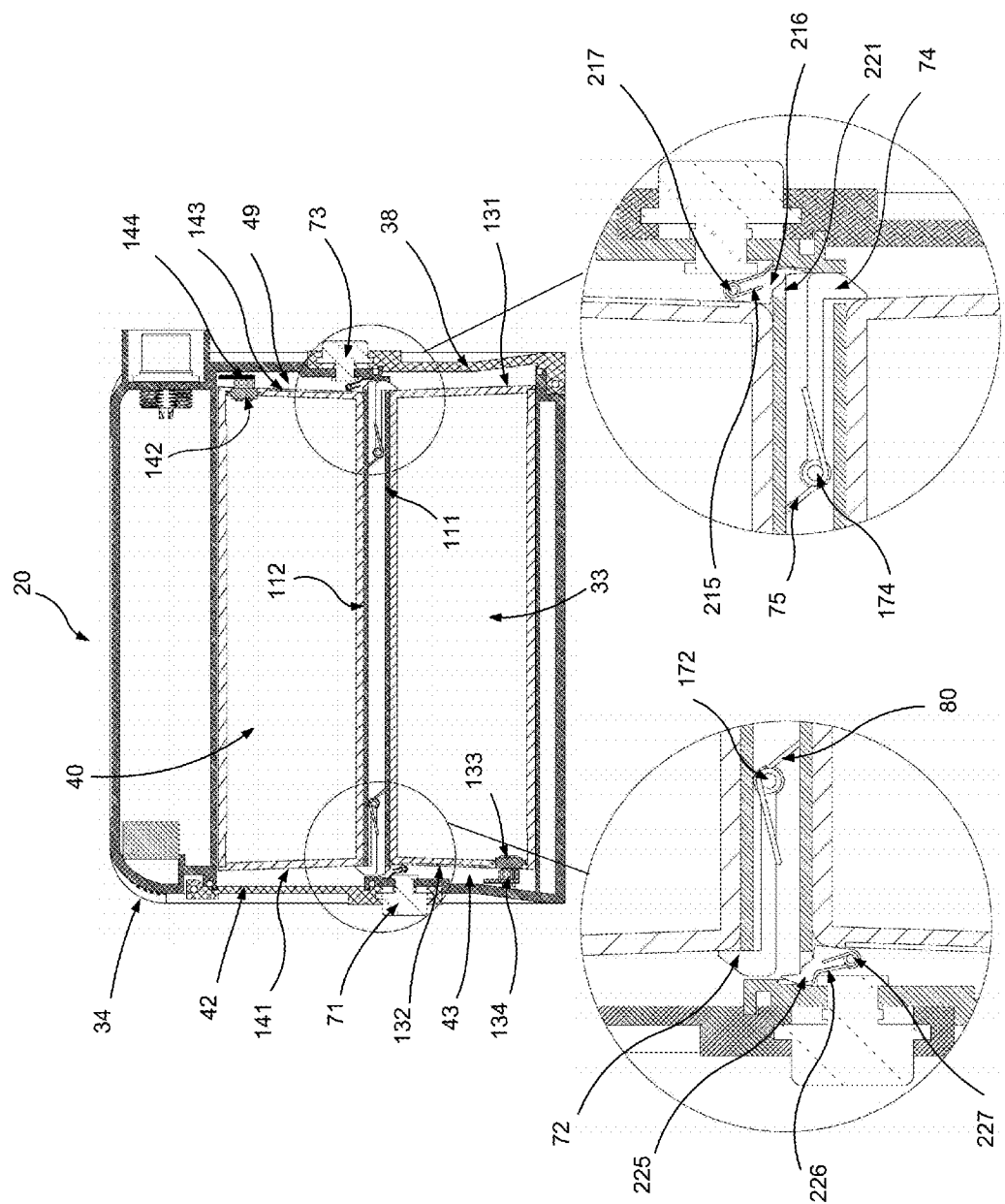

Another example of the locking mechanism for retaining the two or more removable batteries within the controller housing, according to an aspect of the present disclosure, is described with reference to FIGS. 10 through 14. A controller unit 20 includes battery compartments 49, 43, which accommodate the corresponding battery modules 40, 33. Each of the battery compartments has one end open for the battery to enter in, and the other end installed with a receptacle of an electric connector. As shown in FIGS. 10 and 13, when the battery module 40 is completely installed in the battery compartment 49, a plug 142 on the battery module is firmly mated with a corresponding receptacle 144 on the battery compartment 49. The receptacle 144 in turn is coupled to the power management and control circuitry (FIG. 2A) so that the battery module can provide power to the VAD system through the control circuitry.

Figure 14:
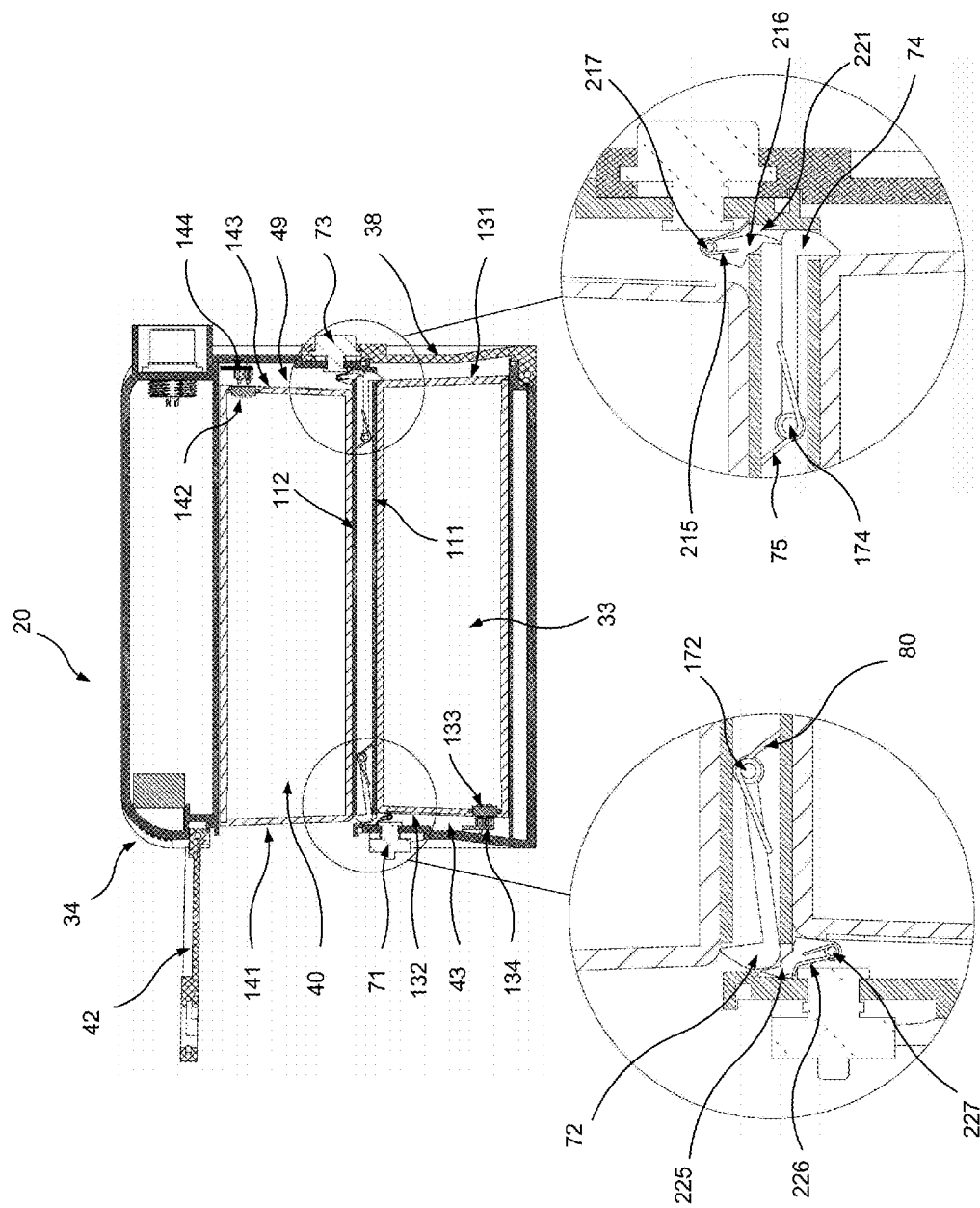

On the opening end of the compartment 49, a latching mechanism is installed to retain the battery 40 in position once it is completely installed. The latching mechanism includes a letch lever 72 loaded by a spring 80, and is installed on the outside of a side wall 102 (FIG. 10) or 112 (FIG. 13) of the compartment 49. The spring 80 urges the latch lever 72 to rotate in such a direction that the latching end of the lever 72 extends into the interior of the compartment 49 through a hole on the side wall of the compartment, as shown in FIGS. 10 and 13. A beveled surface is made on the latch end of the lever 72 to facilitate manual installation of the battery module 40 into the battery compartment 49. When the battery module is being pushed into the compartment, the edge between the end surface 143 and the side surface of the battery module 40 gets in touch with and then presses on the beveled surface of the latch layer 72, and this causes the latch lever to retreat back to allow the battery module passing through. FIGS. 12 and 14 illustrate such a status of the latch lever 72 when the battery module 40 is in the process of being inserted into or removed from the corresponding battery compartment. Once the battery module is completely installed in the compartment, the latch lever 72 closes on the end surface of the battery module 40 and latches the battery module, as shown in FIGS. 10 and 13.

Moreover, if the user wants to remove the battery module from the compartment, the user can unlatch the latching mechanism by manually forcing the latch end of the lever 72 to entirely yield into the hole on the side wall 102 (FIG. 10) or 112 (FIG. 13) of the battery compartment 49.

A substantially identical construction is made for retaining another battery module 33 inside the battery compartment 43, with the corresponding latching mechanism comprising the latch lever 74, spring 75, and pivot point 174. In this example of embodiments of the present disclosure, the batteries 33 and 40 are installed into the corresponding battery compartments from two opposite sides of the controller unit housing. Therefore, the latching mechanisms are located on the two ends of the housing and installed in inverse symmetry with each other, as shown in FIGS. 10 through 14.

The controller unit 20 may involve an interlocking mechanism that prevents the two or more batteries 33 and 40 from being removed from the controller unit at the same time by accident. Examples of the embodiments of such mechanism are described below, but other mechanism can be conceived by people skilled in the art.

In one example, as illustrated in FIG. 10, the housing 34 encloses two battery compartments 43 and 49, which receive two rechargeable batteries 33, 40. One compartment 43 has a side wall 101, which faces a side wall 102 of the other compartment 49. According to aspects of the present disclosure, two inter-locking mechanisms 107, 108 are located in the space between the two walls 101, 102. In this example, the inter-locking mechanisms 107, 108 are identical in construction but installed in inverse symmetry with each other. The inter-locking mechanism 107 includes a two-ended latch lever 78, installed on a hinge 81 that is affixed to the housing 34, and is allowed to rotate freely around the hinge. A spring 79 is installed between the latch lever 78 and the battery compartment wall 101. The spring applies force on the lever 78 to rotate it about the hinge 81 in counter clock wise direction. An opening 341 on the battery compartment wall 101, and an opening 342 on the battery compartment wall 102 allow both ends of the latch lever 78 to extend into the battery compartment 43, 49 if these compartments are not filled with battery modules. One end of the latch level 78 that resides in the opening 342 of the wall of battery compartment 49 serves for latching the battery module installed in the same battery compartment 49, and is named the latching end. The other end that resides in the opening 341 of the wall of the battery compartment 43 serves for constraining rotation of the spring-loaded latch lever 78, and is named the control end. The inter-locking mechanism 108 has substantially the same construction as the inter-locking mechanism 107, and includes latch lever 77, hinge 83, and spring 76. The spring 76 turns the lever 77 in a counter clock wise direction into an opening 344 located on the battery compartment wall 102 and an opening 343 on the battery compartment 101. The latching end of the latch lever 77 resides in the opening 343, and the control end resides in the opening 344.

As illustrated in FIG. 10, when the rechargeable battery module 33 is completely installed in the battery compartment 43, a plug 133 on the battery module 33 securely mates with a receptacle 134 on the battery compartment 43, so that the battery is electrically coupled to the controller unit 20 and is able to deliver power to the VAD system. In the same manner, when the rechargeable battery module 40 is completely installed in the battery compartment 49, a plug 142 mates with a receptacle 144. A latching mechanism including a latch lever 74 and a spring 75 retains the battery module 33 in position when the battery is completely installed. In the same manner, the battery module 40 is retained in position, when completely installed in the battery compartment, by a latching mechanism including a lever 72 and a spring 80. As FIG. 10 shows, a notch 331, 401 is located on each of the rechargeable battery modules 33, 40. When the battery modules 33 and 40 are completely installed in the compartment 43 and 49, the notch 331 on the battery module 33 aligns with the opening 343 on the wall of the battery compartment 43; and the notch 401 on the battery module 40 aligns with the opening 342 on the wall of the battery compartment 49.

When battery module 33 is installed in the corresponding compartment, one of its outer surfaces that touches the side wall 101 of the battery compartment comes into contact with the control end of the latch lever 78, and then pushes the latter towards the outside of the battery compartment 43. As an aspect of the present disclosure, when the battery module 33 is completely installed in the compartment, rotation of the lever 78 due to the spring force from spring 79 is effectively constrained by the outer surface of the battery module 33 so that the latching end of the lever 78 resides entirely inside the opening 342 of the side wall 102 of the battery compartment 49. Therefore, in this situation, the latch lever 78 does not pose any effects on free movement of battery 40 inside the battery compartment 49, i.e., the latch lever 78 is not engaged. With an equivalent design, when battery module 40 is completely installed in the battery compartment 49, one of its outer surfaces comes into contact with the control end of the latch lever 77 that resides in the opening 344 on the wall 102 of battery compartment 49. This constrains rotation of the latch lever 77 due to the spring 76, and causes the latching end of the latch lever 77 to entirely reside inside the opening 343 of the other battery compartment, i.e. the compartment 43. That means that the latch lever 77 is also not engaged and allows free movement of the battery module 33 in the corresponding compartment. Therefore, when the batteries 33, 40 are both completely installed in the corresponding compartments, both of the interlocking mechanisms 107 and 108 are not engaged and any of the battery modules can be freely removed from the compartment.

Figure 11:
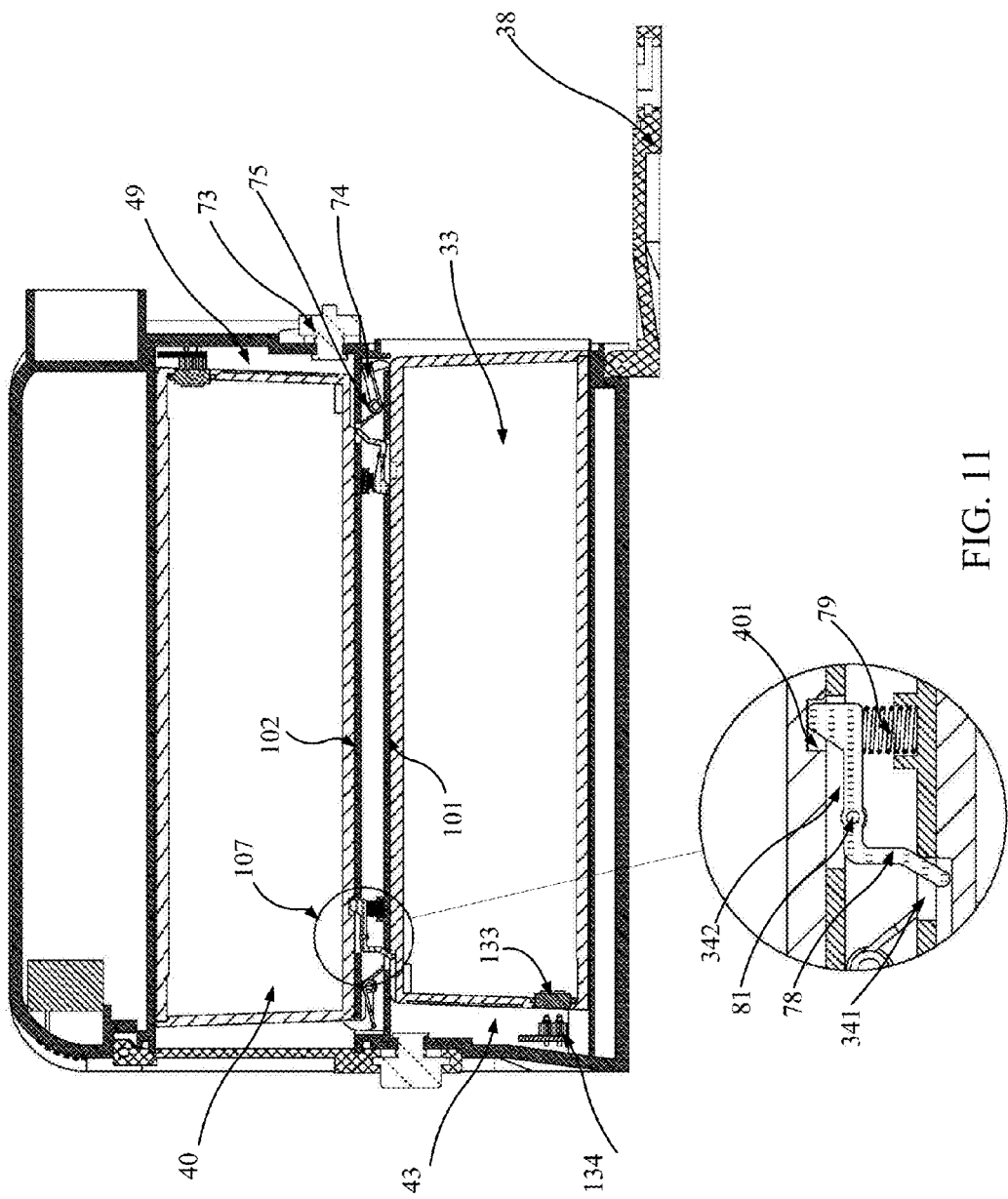

Referring to FIG. 11, when the lid 38 on the battery compartment 43 is opened, the latching mechanism 74 may be released so that the battery 33 is allowed to be removed from the compartment 43. When the battery module 33 is removed from the compartment 43 to an extent that the plug 133 on the battery module is entirely disconnected from the receptacle 134 on the battery compartment 43, the control end of the latch lever 78 passes over the portion of the outer surface of the battery module 33 that constrains rotation of the latch lever. The adjacent portion of the outer surface of the battery module 33 may include a notch, a step, a beveled surface, or any other feature serving the same function that relieves the constraint on rotation of the latch lever. Therefore, once the battery module 33 is disconnected from the receptacle on the corresponding battery compartment, it no longer poses constraint on the latch lever 78. At the same time, the other battery module 40 is completely installed in the battery compartment and thus the notch 401 on the battery module 40 aligns with the opening 342 on the side wall 102 of the battery compartment 49. Therefore, the latch lever 78 is turned by the spring 79 in counter clock wise direction until the latching end goes through the opening 342 and extends into the notch 401 on the battery module 40. This locks the battery module 40 and prevents it from being removed from the battery compartment.

In the same manner and as illustrated in FIG. 12, once battery module 40 is unplugged from the receptacle 144 on the compartment 49, the battery module 33 is locked by the inter-locking mechanism 108 and cannot be removed from the compartment 43.

Another example of embodiments of the interlocking mechanism to prevent two or more batteries from being accidentally removed at the same time is described with reference to FIGS. 13 and 14. A controller unit 20 includes batteries 40, 33 that are installed in corresponding battery compartments 49, 43. Each of the batteries is retained in its compartment with a latching mechanism as previously described. For example, the latching mechanism employs a latch lever 72 to retain the battery module 40 in the corresponding battery compartment 49 once the battery is completely installed. The same latching mechanism is employed in combination with a blocking mechanism to prevent simultaneous removal of two batteries from the compartments. The blocking mechanism is regulated by one of the batteries so that once a battery is unplugged from its connector in a corresponding battery compartment, the blocking mechanism blocks the unlatching movement of a latching mechanism on the other battery. Although particular mechanisms are described herein as examples of the blocking mechanisms, it should be understood that various alternate configurations and mechanisms could be employed by those skilled in the art to implement the embodiments described herein.

Referring to FIGS. 13 and 14, a blocking mechanism including a blocking piece 216, a spring 215 and a pivot point 217, is installed in the battery compartment 49 at the close end of the compartment. The blocking piece 216 has a short and blunt tip, which extends through a hole 221 on the side wall 112 of the battery compartment 49, into the space in between the battery compartments 49 and 43. A latching mechanism including a latch lever 74, a spring 75 and a pivot point 174 is installed in the same space, and serves for retaining a battery module 33 in the battery compartment 43. As shown in FIG. 14, the spring 215 turns the blocking piece 216 in clock wise direction until a side surface of the blocking piece meets the edge of the hole 216. When the blocking piece 216 takes this position, its blunt tip is located right next to the leg of the latching lever 74, and blocks the way for the latching lever to move towards unlatching.

Referring to FIG. 13, a battery 40 is completely installed in the battery compartment 49 so that the plug 142 mates with the receptacle 144. When the battery module is being installed towards this position, the end surface 143 of the battery module gets in touch with and then presses against the side edge of the blocking piece 216, and turns the blocking piece about the pivot point 217 in counter clock wise direction. When the battery module is completely installed, the blocking piece 216 is turned into such a position that its blunt tip sits away from the leg of the latching lever 74 and this clears up the path for unlatching movement of the latching lever 74. Therefore, the blocking mechanism that is regulated by the battery module 40 does not restrict removal of the other battery module, i.e. 33, when the battery module 40 is completely installed in the compartment.

However, as shown in FIG. 14, if the battery 40 is pulled out so that the plug 142 is disconnected with the receptacle 144, then the blocking piece 216 is released from the end surface 143 of the battery module 40. Without such restriction, the blocking piece is turned by the spring 215 in a clockwise direction until its side surface rests on the edge of the hole 216. Therefore, the blocking mechanism that is regulated by the battery module 40 prevents removal of the other battery module, i.e. 33, when the battery module 40 is not completely installed in the compartment.

In addition to the blocking mechanism described above that is installed in one of the battery compartments 49, another blocking mechanism including a blocking piece 225 and a spring 226, is installed in the other battery compartment 33. These two blocking mechanisms are substantially identical in construction and are configured in a symmetrical manner. The two blocking mechanisms together form an interlocking mechanism that prevents removal of the batteries 33, 40 at the same time. The interlocking mechanism provides a safeguard when two or more removable batteries are configured in a controller unit according to an aspect of the present disclosure.

An extra-corporeal controller unit for an implantable ventricular assist device (VAD), according to an aspect of the present disclosure includes a controller unit housing having two or more battery module compartments, control circuitry configured in the control unit housing and a first battery module connector in each of the battery module compartments. The control circuitry is configured for power management, communication, VAD control and VAD monitoring. The battery module connectors are coupled to the control circuitry. The extra-corporeal controller unit also includes two or more battery modules.

According to an aspect of the present disclosure, each battery module is configured for tool-less removability from one of the battery module compartments and configured for tool-less installation in one of the battery module compartments. Each of the battery modules includes a rechargeable battery and a second battery module connector configured for coupling the battery to a corresponding one of the first battery module connectors whenever the battery module is installed in a battery module compartment. The first battery module connectors and the second battery module connectors may include mating conductive contacts or may include contactless coupled coils configured to facilitate power transmission between the first battery module connectors and the second battery module connectors, for example.

According to an aspect of the present disclosure, two or more of the battery modules are configured to independently deliver power to a connector to a percutaneous cable or a transcutaneous energy/signal transmission system on the housing via the control circuitry and to a percutaneous cable or a transcutaneous energy/signal transmission system, respectively, of a ventricular assist device. The control circuitry includes power control circuitry configured to deliver power from a second one of the battery modules to a VAD whenever a first one of the battery modules is removed from the housing or decoupled from a corresponding battery module connector. The power control circuitry is also configured to deliver power from a second one of the battery modules to a VAD whenever available power from a first one of the battery modules is below a predetermined threshold. The extra-corporeal controller unit may also include a display on the housing an indicator corresponding to each of the battery compartments. The display and/or each indicator may be coupled to the control circuitry and configured to indicate a remaining power level of a battery module in the corresponding battery compartment, for example.

Figure 8:
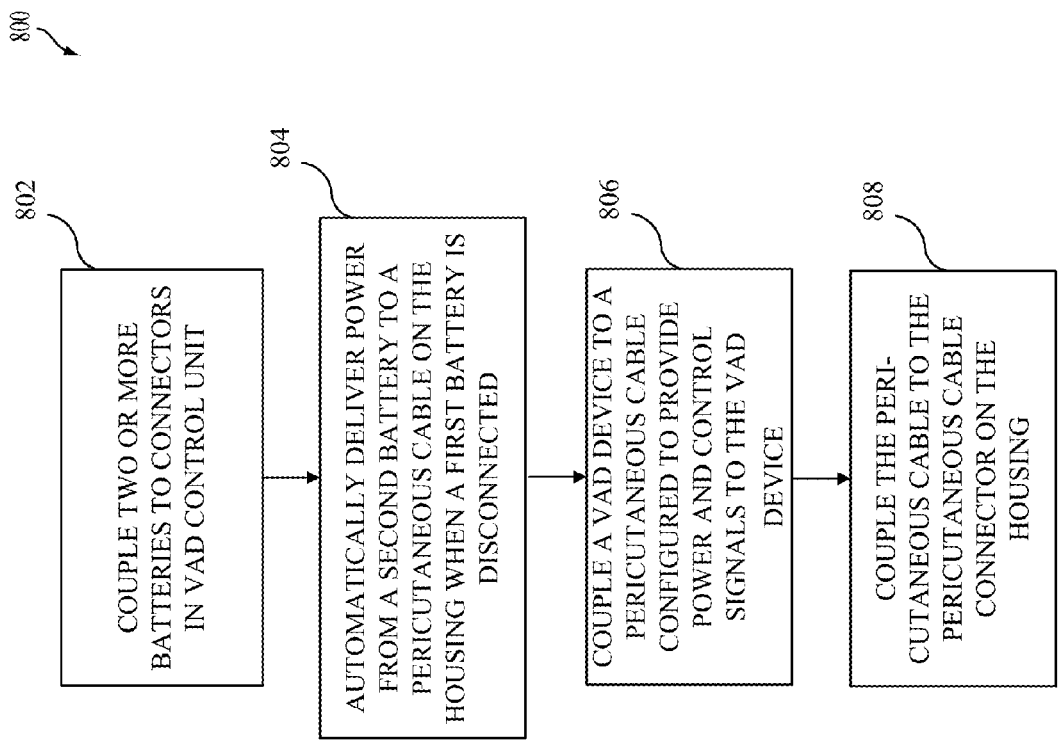
FIG. 8 is a process flow diagram illustrating a method for providing continuous power to a ventricular assist device via a percutaneous cable according to an aspect of the present disclosure.

A method for providing continuous power to a ventricular assist device (VAD) according to another aspect of the present disclosure is described with reference to FIG. 8. The method 800 includes coupling two or more battery modules to corresponding connectors in a VAD control unit housing at block 802, in which each battery module is removably installed in a corresponding battery module compartment of the housing. At block 804, the method includes automatically delivering power from a second one of the battery modules to a percutaneous cable connector on the housing whenever a first one of the battery modules is removed from the housing or decoupled from a corresponding battery module connector. At block 806, the method includes coupling a VAD device to a percutaneous cable configured to provide power and control signals to the VAD device. At block 808, the method includes coupling the percutaneous cable to the percutaneous cable connector on the housing.

According to aspects of the present disclosure, the VAD controller unit includes only one extra-corporeal component to be carried by patient. No extra cables other than the percutaneous cables are needed to operate the VAD. This increases patient's mobility and comfort. Elimination of the extra cables and connectors also reduces risk of failure due to mechanical wear of connectors and accidental detachment of a connector. According to aspects of the present disclosure, two or more batteries can independently supply power to the circuitry and/or to the VAD. When one of the batteries is removed or out of capacity, the VAD can still be powered by the remaining battery as long as the remaining battery is connected and functioning.

Figure 9:
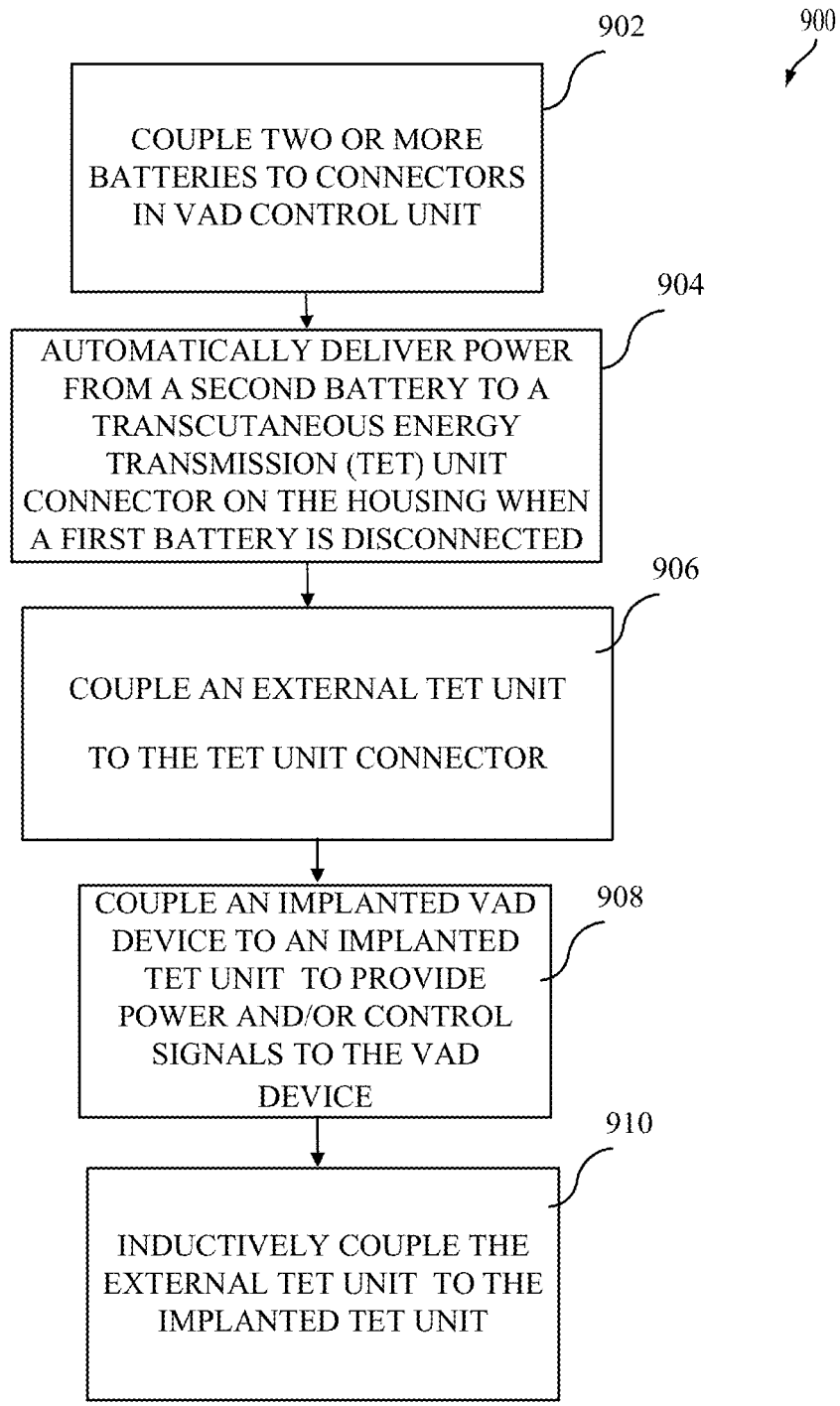
FIG. 9 is a process flow diagram illustrating a method for providing continuous power to a ventricular assist device via inductively coupled transcutaneous energy transmission units according to an aspect of the present disclosure.

A method for providing continuous power to a ventricular assist device (VAD) according to another aspect of the present disclosure is described with reference to FIG. 9. The method 900 includes coupling two or more battery modules to corresponding connectors in a VAD control unit housing at block 902, in which each battery module is removably installed in a corresponding battery module compartment of the housing. At block 904, the method includes automatically delivering power from a second one of the battery modules to a transcutaneous energy transmission (TET) unit connector on the housing whenever a first one of the battery modules is removed from the housing or decoupled from a corresponding battery module connector. At block 906, the method includes coupling an external TET unit to the TET unit connector. At block 908, the method includes coupling an implanted VAD device to an implanted TET unit configured to provide power and/or control signals to the VAD device. At block 910, the method includes inductively coupling the external TET unit to the implanted TET unit.

As used herein, the term "coupled" or "communicably coupled" can mean any physical, electrical, magnetic, or other connection, either direct or indirect, between two parties. The term "coupled" is not limited to a fixed direct coupling between two entities. The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. An extra-corporeal controller unit for a ventricular assist device (VAD) that includes a housing having first and second battery module compartments with respective first and second battery modules adapted to provide power to the VAD, the controller unit comprising:

control circuitry configured for managing power provided from the first and second battery modules to the VAD;

first and second battery module connectors operably coupled to the control circuitry and respectively operably coupled to the first and second battery modules;

an interlocking mechanism adapted to prevent operably decoupling the first battery module connector from the first battery module if the second battery module connector is not operably coupled to the second battery module; and a connector adapted to operably couple the control circuitry to a percutaneous cable or a transcutaneous energy transmission (TET) unit.

2. The controller unit of claim 1, wherein
each of the first and second battery modules is configured for tool-less removal from and installation in the respective first and second battery module compartments, and the first and second battery modules each includes a rechargeable battery.

3. The controller unit of claim 2, wherein the control circuitry is configured to cause the second battery module to provide power to the VAD when the first battery module is operably decoupled from the first battery module connector, or when power provided from the first battery module to the VAD is below a preset threshold.

4. The controller unit of claim 1, wherein the control circuitry is configured to cause the second battery module to provide power to the VAD in response to detecting an abnormal functioning of the first battery module.

5. The controller unit of claim 1,
wherein the second battery module has a smaller power capacity than the first battery module, and
the control circuitry is configured to cause the second battery module to provide power to the VAD when the first battery module is operably decoupled from the first battery module connector, or when power provided from the first battery module to the VAD is below a preset threshold.

6. The controller unit of claim 2, wherein the control circuitry is configured to cause the second battery module to provide power to the VAD when a first capacity of power of the first battery module falls below a first capacity threshold, and the second battery module possesses a second capacity of power above a second capacity threshold, which is greater than the first capacity threshold.

7. The controller unit of claim 6, wherein the control circuitry is configured to cause a reminder signal to inform a user to change the first battery module.

8. The controller unit of claim 6, wherein the control circuitry is configured to cause a warning signal to inform a user to change the first battery module when the first battery module falls below a third capacity threshold, wherein a difference between the first capacity threshold and the third capacity threshold is an amount of time for the second capacity to decrease to the first capacity threshold sufficient for the user to change the first battery module.

9. The controller unit of claim 1, further comprising a second connector adapted to operable couple the control circuitry to an external power source.

10. An extra-corporeal controller unit for a ventricular assist device (VAD) that includes a housing having first and second battery module compartments with respective first and second battery modules adapted to provide power to the VAD, the controller unit comprising:

control circuitry configured for managing power provided from the first and second battery modules to the VAD;

an energy storage unit permanently operably coupled to the control circuitry;

first and second battery module connectors respectively in the first and second battery module compartments and respectively operably coupled to the first and second battery modules, wherein each of the first and second battery module connectors is operably coupled to the control circuitry;

an interlocking mechanism adapted to prevent operably decoupling of the first battery module connector from the first battery module if the second battery module connector is not operably coupled to the second battery module; and a connector adapted to operably couple the control circuitry to a percutaneous cable or a transcutaneous energy transmission (TET) unit.

11. The controller unit of claim 10, wherein
each of the first and second battery modules is configured for tool-less removal from and installation in the respective first and second battery module compartments.

12. The controller unit of claim 11, wherein the control circuitry is configured to cause power from the energy storage unit to be delivered to at least one of the control circuitry and the VAD when the first and second battery modules connectors are respectively operably decoupled from the first and second battery modules, or when power provided from the first and second battery modules to the VAD is below a preset threshold.

13. The controller unit of claim 11, wherein the control circuitry is configured to cause the second battery module to provide power to the VAD when the first battery module connector is operably decoupled from the first battery module, or when power provided from the first battery module is below a preset threshold.

14. The controller unit of claim 10, wherein the control circuitry is configured to switch power provided to the VAD from one of the first battery module, the second battery module, or the energy storage unit in operation, to another of the first battery module, the second battery module, or the energy storage unit not in operation in response to detecting an abnormal functioning of the one of the first battery module, the second battery module, or the energy storage unit in operation to ensure an uninterrupted amount of power is supplied to the VAD.

15. The controller unit of claim 10, wherein
the second battery module has a smaller power capacity than the first battery module, and
the control circuitry is configured to cause the second battery module to deliver power to the VAD if the first battery module connector is operably decoupled from the first battery module, or when power delivered from the first battery module is below a preset threshold.

16. The controller unit of claim 10, wherein the energy storage unit includes a super-capacitor or a backup battery.

17. The controller unit of claim 11, wherein the control circuitry is configured to switch power delivered to the VAD from the first battery module to the second battery module when a first capacity of power of the first battery module falls below a first capacity threshold, and the second battery module possesses a second capacity of power above a second capacity threshold, which is greater than the first capacity threshold.

18. The controller unit of claim 17, wherein the control circuitry is configured to cause a reminder signal to inform a user to change the first battery module.

19. The controller unit of claim 17, wherein the control circuitry is configured to cause a warning signal to inform a user to change the first battery module when the first battery module falls below a third capacity threshold, wherein a difference between the first capacity threshold and the third capacity threshold is an amount of time for the second capacity of the second battery module to decrease to the first capacity threshold sufficient for the user to change the first battery module.

20. The controller unit of claim 10, further comprising:
a second connector on the housing adapted to couple the control circuitry to an external power source.

* * * * *